United States Patent [19]

Whaley et al.

[11] 4,427,776

[45] Jan. 24, 1984

[54] COMPOSITION OF MATTER AND PROCESS

[75] Inventors: Howard A. Whaley; William C. Snyder; John C. Greenfield, all of Portage; John H. Coats, Kalamazoo, all of Mich.

[73] Assignee: The Upjohn Company, Kalamazoo, Mich.

[21] Appl. No.: 304,393

[22] Filed: Sep. 21, 1981

[51] Int. Cl.³ .................... C12P 1/06; A61K 35/00
[52] U.S. Cl. ................................. 435/169; 424/122
[58] Field of Search ..................... 424/122; 435/169

[56] References Cited

PUBLICATIONS

Mallams, A. K. et al., J. Am. Chem. Soc. 103, 3938, 3940, (1981).

Kobinata, K., et al., J. Antib. 33, 244, (1980).
Isono, K. et al., J. Antib. 33, 772, (1980).
Tomita, F. et al., J. Antib. 33, 668, (1980).
Tamaoki, T. et al., J. Antib. 33, 946, (1980).

Primary Examiner—Jerome D. Goldberg
Attorney, Agent, or Firm—Roman Saliwanchik

[57] ABSTRACT

Novel antibiotic U-64,815 producible in a fermentation under controlled conditions using a biologically pure culture of the microorganism *Streptomyces microspinus*, NRRL 12524. This antibiotic is active against various Gram-positive bacteria, for example, *Staphylococcus aureus*. It is also active against *Haemophilus influenzae*. Thus, antibiotic U-64,815 can be used in various environments to eradicate or control such bacteria.

2 Claims, 3 Drawing Figures

COMPOSITION OF MATTER AND PROCESS

BACKGROUND OF THE INVENTION

Antibiotic U-64,815 can be differentiated from the known related antibiotics kijanimicin [A. K. Mallams, et al., J. Amer. Chem. Soc. 103, 3938, 3940 (1981)], antlermicins [K. Kobinata, et al., J. Antibiotics 33, 244 (1980); K. Isono, et al., ibid., 33, 772 (1980)] and tetrocarcins [F. Tomita, et al., J. Antibiotics 33, 668 (1980); T. Tamaoki, et al., ibid., 33, 946 (1980)] on the basis of observed $^{13}C$ magnetic resonance spectra. Compound 12 disclosed in the J.A.C.S. article, appears to be identical to antibiotic U-64,815. Final resolution of this identity is in progress.

BRIEF SUMMARY OF THE INVENTION

Antibiotic U-64,815 is producible in a fermentation under controlled conditions using a biologically pure culture of the new microorganism *Streptomyces microspinus*, NRRL 12524.

Antibiotic U-64,815 has moderate to excellent in vitro activity against all strains of *Haemophilus influenzae* tested. It is also active against various Gram-positive bacteria. Further, the base addition salts of antibiotic U-64,815 are also active against these bacteria. Thus, antibiotic U-64,815 and its salts can be used to disinfect washed and stacked food utensils contaminated with *S. aureus*. They can also be used as disinfectants on various dental and medical equipment contaminated with *S. aureus*. Still further, antibiotic U-64,815 and its salts can be used as a bacteriostatic rinse for laundered clothes, and for impregnating papers and fabrics; and, they are also useful for suppressing the growth of sensitive organisms in plate assays and other microbiological media.

DETAILED DESCRIPTION OF THE INVENTION

Chemical and Physical Properties of Antibiotic U-64,815:

Molecular Weight Range: 1,104–1,324 (based on molecular formula).

Molecular Formula: $C_{60-65}H_{82-102}N_{1-3}O_{18-25}$.

Figure 2:
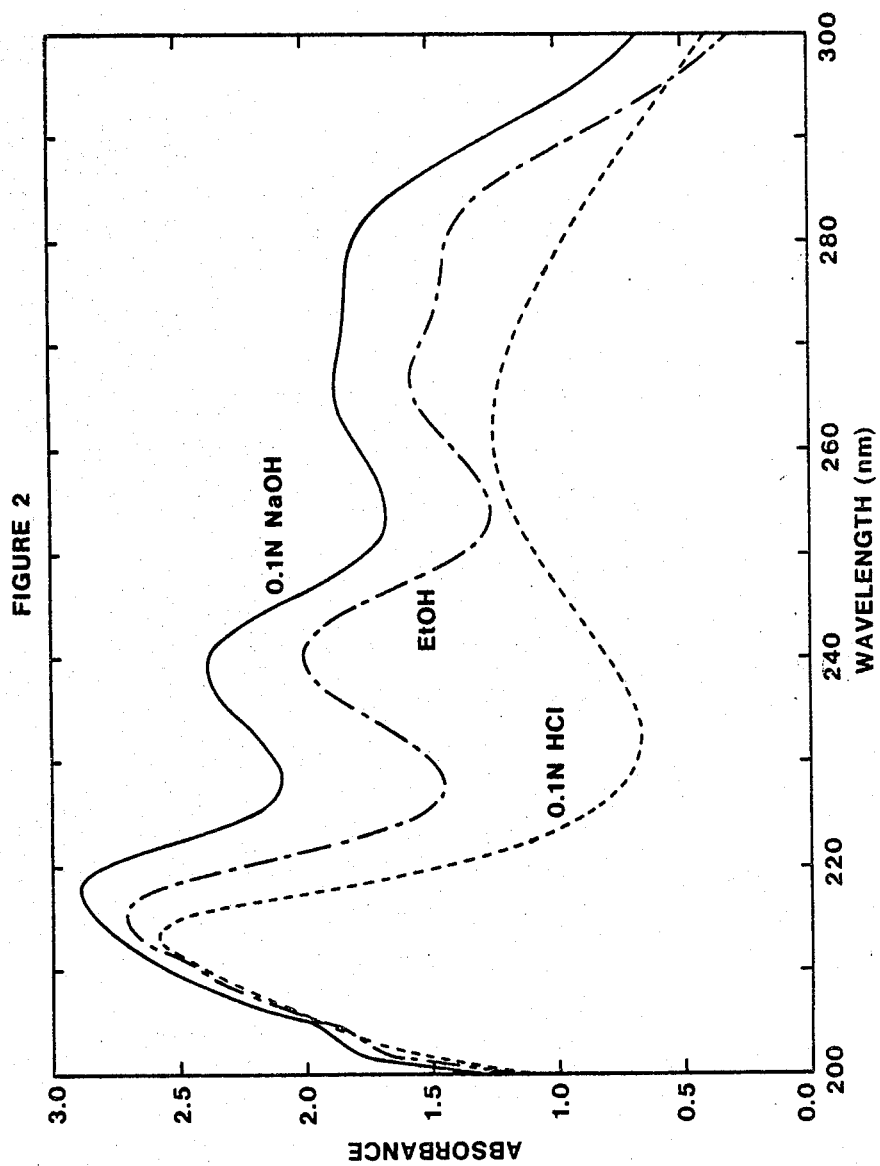

Ultraviolet Absorption Spectrum:

The UV spectrum of antibiotic U-64,815 is shown in FIG. 2 of the drawings. The solution of antibiotic U-64,815 in ethanol displayed absorption as follows:

| Solvent | λ max |
|---|---|
| Ethanol | 215 |
|  | 240 |
|  | 267 |
|  | 278 (sh) |
| .1 N HCl | 213 |
| in Ethanol | 261 |

Melting Point: 185–187 (dec)

Figure 1:
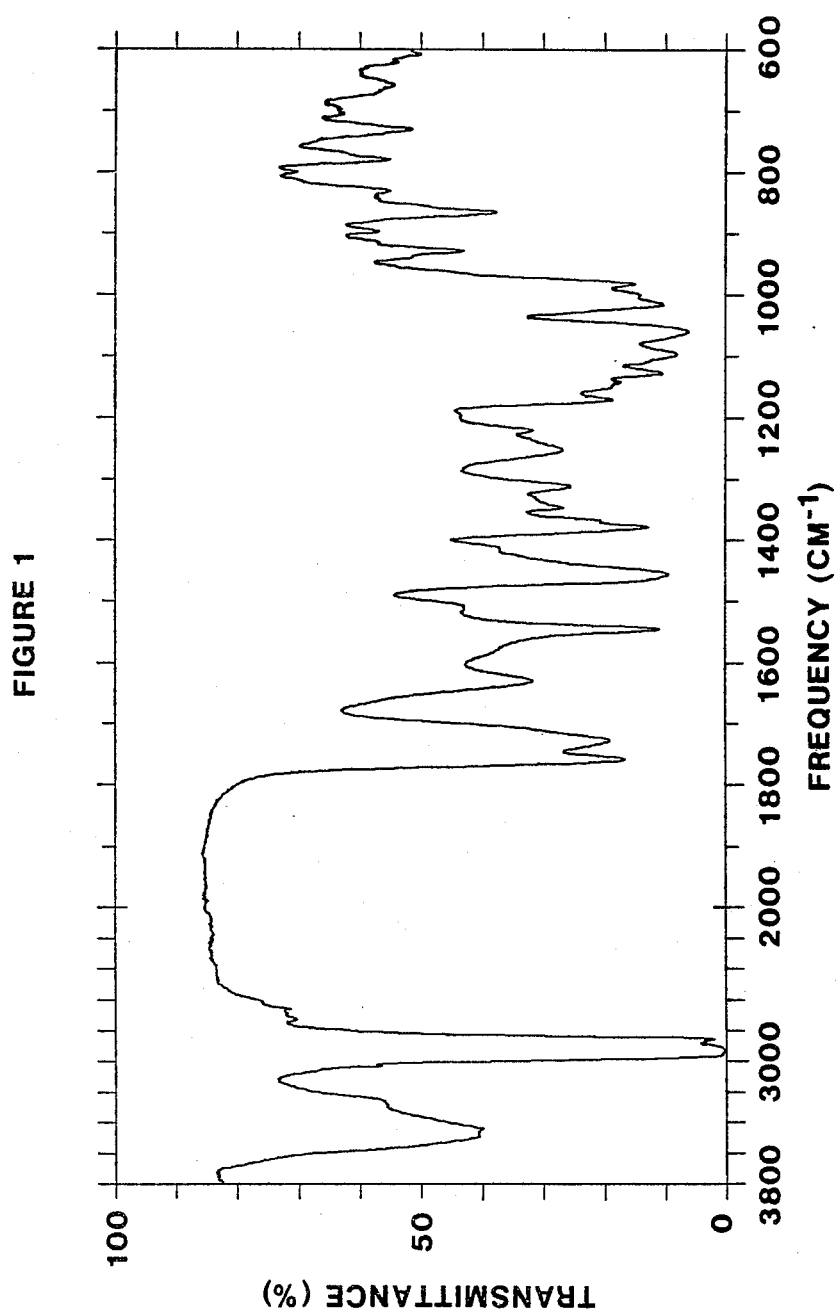

Infrared Absorption Spectrum:

Antibiotic U-64,815 has a characteristic infrared absorption spectrum in a mineral oil mull as shown in FIG. 1 of the drawings. Peaks are observed at the following wave lengths:

| Band Freq. | Inten. | Type |   | Band Freq. | Inten. | Type |   |
|---|---|---|---|---|---|---|---|
| 3480.0 | 40 | SH | * | 1196.9 | 43 | BRD |   |
| 3442.3 | 40 | BRD |   | 1170.9 | 18 | AVG |   |
| 3280.0 | 56 | SH | * | 1149.7 | 18 | SH |   |
| 3058.5 | 67 | SH |   | 1141.9 | 17 | AVG |   |
| 3025.7 | 56 | AVG |   | 1127.5 | 10 | AVG |   |
| 2956.2 | 0 | BRD | M | 1095.6 | 8 | AVG |   |
| 2931.1 | 0 | BRD | M | 1059.0 | 6 | AVG |   |
| 2870.4 | 3 | BRD | M | 1014.6 | 10 | AVG |   |
| 2854.0 | 2 | AVG | M | 1000.2 | 14 | AVG |   |
| 2726.7 | 70 | BRD | M | 981.8 | 14 | AVG |   |
| 2661.1 | 71 | AVG |   | 936.5 | 51 | SH |   |
| 2617.7 | 76 | SH |   | 927.8 | 43 | SHP |   |
| 1760.2 | 16 | AVG |   | 914.3 | 56 | AVG |   |
| 1729.3 | 19 | AVG |   | 897.0 | 56 | SHP |   |
| 1629.0 | 31 | AVG |   | 865.1 | 37 | AVG |   |
| 1575.0 | 37 | SH | * | 831.4 | 55 | AVG |   |
| 1544.2 | 10 | AVG |   | 800.5 | 70 | AVG |   |
| 1510.4 | 43 | AVG |   | 779.3 | 55 | AVG |   |
| 1455.4 | 9 | AVG | M | 730.1 | 51 | AVG |   |
| 1413.9 | 37 | AVG |   | 704.1 | 62 | AVG |   |
| 1378.3 | 12 | AVG | M | 667.4 | 57 | SH |   |
| 1366.7 | 20 | AVG |   | 656.8 | 54 | AVG |   |
| 1346.4 | 26 | AVG |   | 619.2 | 54 | SH |   |
| 1311.7 | 25 | AVG |   | 607.6 | 50 | AVG |   |
| 1250.9 | 26 | AVG |   |   |   |   |   |
| 1220.1 | 31 | AVG |   |   |   |   |   |

Band Freq.: Band Frequencies in Wavenumbers ($CM^{-1}$)
Inten.: Intensity in Percent Transmittance (% T)
Date Type in Local Peak Region:
BRD = Broad;
AVG = Average;
SHP = Sharp;
SH = Shoulder
Peak List Edited.
* Indicates Peaks Added.
M: Possible Interference from Mineral Oil.

Antibiotic U-64,815 has a characteristic infrared absorption spectrum when passed into a KBr pellet. Peaks are observed at the following wave lengths:

| Band Freq. | Inten. | Type |   | Band Freq. | Inten. | Type |   |
|---|---|---|---|---|---|---|---|
| 3480.0 | 32 | SH | * | 1170.9 | 27 | AVG |   |
| 3441.4 | 30 | BRD |   | 1141.0 | 26 | AVG |   |
| 3259.1 | 52 | SH |   | 1126.5 | 18 | AVG |   |
| 3029.5 | 55 | AVG |   | 1096.6 | 14 | AVG |   |
| 2971.6 | 31 | AVG |   | 1058.0 | 11 | AVG |   |
| 2931.1 | 16 | AVG |   | 1014.6 | 16 | AVG |   |
| 2911.8 | 24 | SH |   | 999.2 | 20 | AVG |   |
| 2852.0 | 36 | SHP |   | 981.8 | 21 | AVG |   |
| 2799.0 | 66 | SH |   | 937.5 | 55 | AVG |   |
| 2662.0 | 67 | AVG |   | 927.8 | 50 | AVG |   |
| 1761.2 | 25 | AVG |   | 913.4 | 60 | SH |   |
| 1734.2 | 27 | AVG |   | 897.0 | 59 | AVG |   |
| 1631.0 | 33 | AVG |   | 865.1 | 46 | AVG |   |
| 1577.9 | 41 | SH |   | 843.9 | 60 | AVG |   |
| 1545.1 | 18 | SHP |   | 831.4 | 59 | AVG |   |
| 1508.5 | 43 | AVG |   | 800.5 | 67 | AVG |   |
| 1451.6 | 28 | AVG |   | 778.3 | 59 | AVG |   |
| 1434.2 | 39 | SH |   | 732.0 | 59 | AVG |   |
| 1413.9 | 42 | AVG |   | 706.0 | 65 | AVG |   |
| 1384.0 | 31 | AVG |   | 667.4 | 60 | SH |   |
| 1382.1 | 31 | SH |   | 657.8 | 59 | AVG |   |
| 1368.6 | 34 | AVG |   | 618.2 | 61 | SH |   |
| 1346.4 | 36 | AVG |   | 607.6 | 58 | AVG |   |
| 1310.7 | 36 | AVG |   | 507.3 | 60 | AVG |   |
| 1249.0 | 39 | BRD |   | 489.0 | 59 | AVG |   |
| 1235.5 | 40 | BRD |   | 430.0 | 52 | AVG | * |

-continued

| Band Freq. | Inten. | Type | Band Freq. | Inten. | Type |
|---|---|---|---|---|---|
| 1221.0 | 37 | AVG | | | |

Band Freq.: Band Frequencies in Wavenumbers (CM$^{-1}$)
Inten.: Intensity in Percent Transmittance (% T)
Date Type in Local Peak Region:
BRD = Broad;
AVG = Average;
SHP = Sharp;
SH = shoulder
Peak List Edited.
* Indicates Peaks Added.

Figure 3:
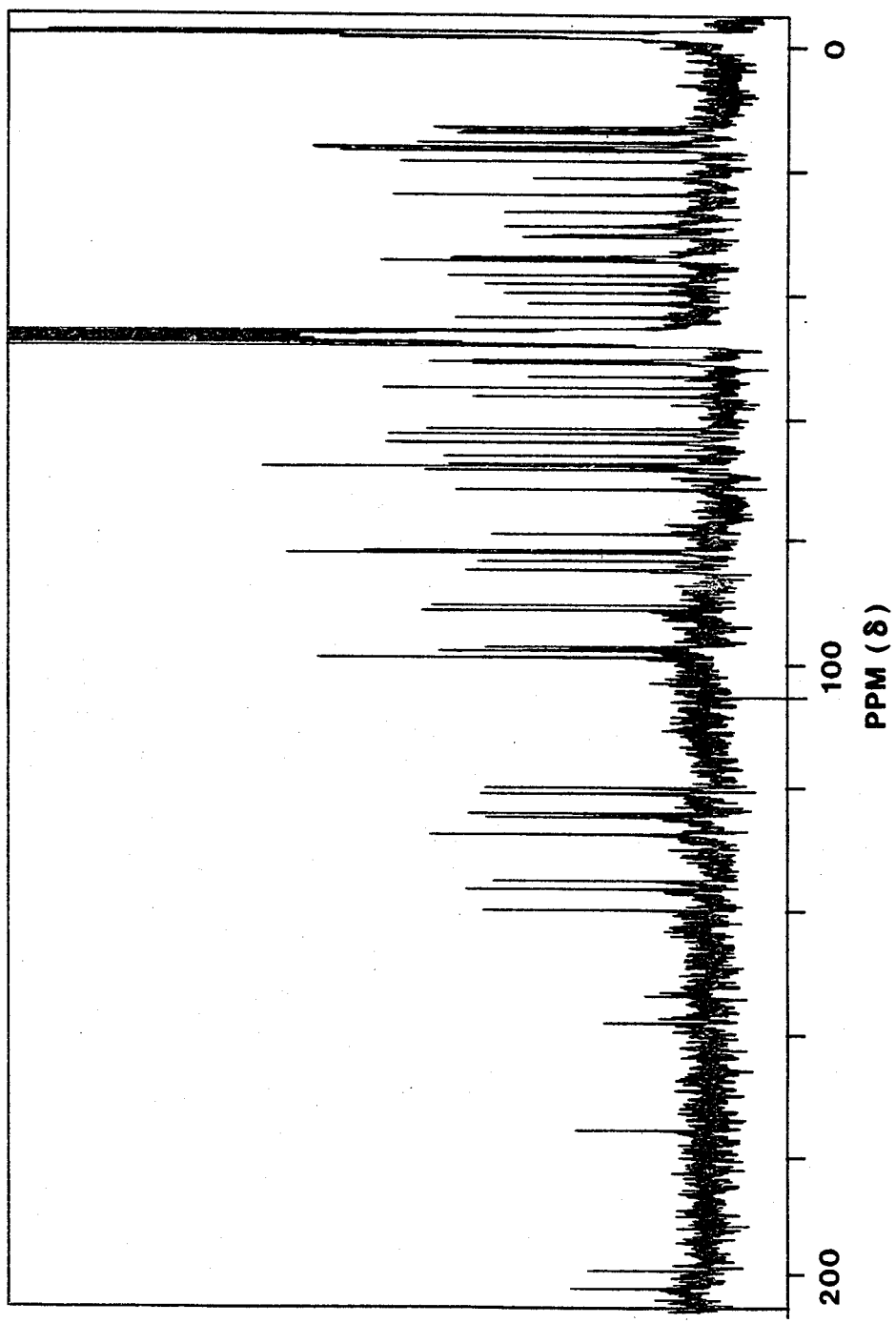

$^{13}$C-Nuclear Magnetic Resonance (NMR) Spectrum:

The $^{13}$C-NMR spectrum of antibiotic U-64,815 is shown in FIG. 3 of the drawings. The $^{13}$C-NMR spectrum was observed on a Varian XL-200 Spectrometer (50 mHz) on a solution (ca. 0.5 ml., ca. 40 mg/ml) of the sample of the antibiotic in deutero-methanol. The spectrum was calibrated against internal tetramethylsilane and frequencies were recorded in ppm downfield from tetramethylsilane.

Solubilities:

Antibiotic U-64,815 is soluble in methanol acetone, methylene chloride, ethanol and dimethylsulfoxide. It is insoluble in water and hexane.

Antimicrobial Spectrum of Antibiotic U-64,815:

Antibiotic U-64,815 is active against various Gram-positive bacteria and H. influenzae as shown in the following table.

Assay:

The antibacterial assay is a standard disc plate assay. Ten 6.35 mm absorbent discs are saturated with a 1000 μg/ml solution prepared in methanol (solvent) and air-dried prior to spotting on organism-seeded agar plates. The results are as follows:

| | | Zone Size (mm) |
|---|---|---|
| Haemophilus influenzae (Ampicillin-susceptible) | UC 6482 | 10 |
| Haemophilus influenzae (Ampicillin-resistant) | UC 6483 | 9 |
| Streptococcus pyogenes | UC 152 | 13 |
| Streptococcus pneumoniae | UC 41 | 16 - outer ring 10 - inner ring |
| Staphylococcus aureus (Multiple antibiotic-resistant) | UC 6685 | 8 |
| Staphylococcus aureus (Multiple antibiotic-resistant) | UC 6690 | 8 - light |
| N. gonorrhoeae | UC 3065 | 16 |

"UC" is a registered trademark of The Upjohn Company Culture Collection. These cultures can be obtained from The Upjohn Company in Kalamazoo, Mich., upon request.

THE MICROORGANISM

The microorganism used for the production of antibiotic U-64,815 is a biologically pure culture of *Streptomyces microspinus*, NRRL 12524.

A subculture of this microorganism can be obtained from the permanent collection of the Northern Regional Research Laboratory, U.S. Department of Agriculture, Peoria, Ill., U.S.A. Its accession number in this depository is NRRL 12524. It should be understood that the availability of the culture does not constitute a license to practice the subject invention in derogation of patent rights granted with the subject instrument by governmental action.

The microorganism of this invention was studied and characterized by Alma Dietz of The Upjohn Research Laboratories.

*Streptomyces microspinus*, Dietz sp. nov. ["microspinus" denotes the small spines found on the surface of the spores], appeared most similar on Ektachrome (Table 1) to *Streptomyces impexus* NRRL 3809, which is described in Goldstein and Prokop [Goldstein, A. W. and J. F. Prokop. 1972. Antibiotic effective against gram-positive bacteria and method of preparation. U.S. Pat. No. 3,651,217], and *Streptomyes fungicidicus* ATCC®21013, which is described in Shibata et al [Shibata, M., E. Higashide, K. Hatano, K. Mizuno, M. Asai, and M. Muroi. 1974. Antibiotic enduracidin and process for the production thereof. U.S. Pat. No. 3,786,142]. All the cultures have open spiral chains of spores with spiny surfaces. *S. impexus* and *S. fungicidicus* have abundant chains of flexuous spore chains as well as open-spiral spore chains. The spines on spores of these cultures are more readily apparent than those on spores of *Streptomyces microspinus*. All cultures are melanin-negative. All have gray aerial growth when the surface color is matched with the NBS color chips [SRM 2106. ISCC-NBS Centroid Color Charts. Office of Standard Reference Material, Room B311, Chem. Building, National Bureau of Standards, Washington, D.C. 20234], but only *Streptomyces microspinus* belongs to the Gray series of Tresner and Backus [Tresner, H. D., and E. J. Backus. 1963. System of color wheels for streptomycete taxonomy. Appl. Microbiol. 11:335–338]. *Streptomyces microspinus* is further distinguished from *S. impexus* and *S. fungicidicus* by its growth on carbon compounds (Table 3) in the synthetic medium of Shirling and Gottlieb [Shirling, E. B., and D. Gottlieb. 1966. Methods for characterization of Streptomyces species. Int. J. Syst. Bacteriol. 16:313–340] and by its general cultural characteristics (Table 4). The new culture grows well in the temperature range of 18°–55° C.; the other cultures do not grow at 45°–55° C. The new culture produces the antibiotic U-64815; *S. impexus* produces M-411 and *S. fungicidicus* produces Enduracidin. It can also be differentiated from cultures in the Gray spiral, melanin-negative, spiny spore group in Bergey's Manual, 8th ed. [Pridham, T. G., and H. D. Tresner. 1974. Part 17. Actinomycetes and related organisms. Family VII. Streptomycetaceae Waksman and Henrici 1943. Genus I. Streptomyces Waksman and Henrici 1943. Table 17.42h of the Gray series. Pages 782–785 in Buchanan and Gibbons, eds., Bergey's Manual of Determinative Bacteriology, 8th ed. The Williams and Wilkins Co., Baltimore]. Therefore, it is proposed that *Streptomyces microspinus* be considered a new species of the actinomycete genus Streptomyces. It is understood that in accordance with the Rules of Nomenclature of Bacteria [Lapage, S. P., P. H. A. Sneath, E. F. Lessel, V. B. D. Skerman, H. P. R. Seeliger, and W. A. Clark, ed. 1975. International code of nomenclature of bacteria, 1976 Revision. American Society for Microbiology, Washington, D.C.], this is the type strain and that, should another strain be found, the type strain would also be the type subspecies.

*Streptomyces microspinus* Dietz sp. nov. NRRL 12524.

Color Characteristics: Aerial mycelium prednominantly gray. Melanin-negative. The color pattern of the culture on Ektachrome is given in Table 1. Reference color characteristics are given in Table 2. The culture may be placed in the Gray (GY) color series of Tresner and Backus [Tresner, H. D., and E. J. Backus, Ibid.].

Microscopic Characteristics: Spore chains are predominantly open-spiral. Spores are oval, 1.1×0.76 μm. Many spores have depressions like those of red blood cells; others have a double collapsed appearance which gives a ridged appearance. The surface of the spores is covered with blunt spines. Spore surface detail is best determined at magnifications of 10,000 to 20,000 with the scanning electron microscope. Fourteen day cover glass preparations were used for the microscopic examinations.

Growth on Carbon Compounds: See Table 3.

Whole Cell Analysis: L-diaminopimelic acid was detected.

Culture Characteristics-General: See Table 4.

Temperature: Growth was good at 18°–55° C. on Czapek's sucrose and Maltose-tryptone agars and at 18°–45° C. on Bennett's agar.

Source: Kansas soil.

Type Strain: *Streptomyces microspinus* sp. nov. NRRL 12524.

TABLE 1

| | | Color Characteristics* on Ektachrome** | | | | | |
|---|---|---|---|---|---|---|---|
| | Determination | S. microspinus NRRL 12524 | | S. impexus NRRL 3809 | | S. fungicidicus ATCC 21013 | |
| Agar Medium | | Chip | Color | Chip | Color | Chip | Color |
| Bennett's | S | 233 | pale gray | 32 | grayish yellowish pink | 70 | light orange yellow |
| | R | 72 | dark orange yellow | 70 | light orange yellow | 70 | light orange yellow |
| Czapek's sucrose | S | 233 | pale gray | 32 | grayish yellowish pink | 9 | pink white |
| | R | 32 | grayish Yellowish pink | 32 | grayish yellowish pink | 9 | pink white |
| Maltose-tryptone | S | 233 | pale gray | 31 | pale yellow pink | 7 | pale pink |
| | R | 72 | dark orange yellow | 67 | brilliant orange yellow | 68 | strong orange yellow |
| Peptone-iron | S | 71 | moderate orange yellow | 32 | grayish yellowish pink | 71 | moderate orange yellow |
| | R | 68 | strong orange yellow | 68 | strong orange yellow | 68 | strong orange yellow |
| 0.1% Tyrosine | S | 32 | grayish yellowish pink | 32 | grayish yellowish pink | 7 | pale pink |
| | R | 38 | dark reddish orange | 38 | dark reddish orange | 38 | dark reddish orange |
| Casein starch | S | 233 | pale gray | 32 | grayish yellowish pink | 10 | pinkish gray |
| | R | 93 | yellowish gray | 76 | light yellowish brown | 93 | yellowish gray |

S = Surface
R = Reverse
*Growth on media in tubes was photographed after seven days incubation at 28° C. Color was determined by comparison with NBS color chips [SP 440. Color: Universal Language and Dictionary of Name. U.S. Government Printing Office, Washington, D.C. 20402; SRM 2106. Ibid.].
**Dietz, A. 1954. Ektachrome transparencies as aids in actinomycete classification. Ann. N.Y. Acad. Sci. 60:152-154 and Dietz, A. and D. W. Thayer (ed.). 1980. Actinomycete Taxonomy (Procedures for Studying Aerobic Actinomycetes with Emphasis on the Streptomycetes). SIM Special Publication Number 6. Soc. for Ind. Microbiol. Arlington, VA.

TABLE 2

| | | Reference Color Characteristics* | | | | | |
|---|---|---|---|---|---|---|---|
| | Determination | S. microspinus NRRL 12524 | | S. impexus NRRL 3809 | | S. fungicidius ATCC 21013 | |
| Agar Medium | | Chip | Color | Chip | Color | Chip | Color |
| Bennett's | S | 266 | dark gray | 90 | grayish yellow | 90 | grayish yellow |
| | R | 58 | moderate brown | 90 | grayish yellow | 70 | light orange yellow |
| | P | 71 | moderate orange yellow | — | — | — | — |
| Czapek's sucrose | S | 45 | light grayish reddish brown | 63 | light brownish gray | 63 | light brownish gray |
| | R | 93 | yellowish gray | 73 | pale orange yellow | 73 | pale orange yellow |
| | P | — | — | — | — | — | — |

TABLE 2-continued

| | | Reference Color Characteristics* | | | | | |
|---|---|---|---|---|---|---|---|
| | Deter- mina- | S. microspinus NRRL 12524 | | S. impexus NRRL 3809 | | S. fungicidius ATCC 21013 | |
| Agar Medium | tion | Chip | Color | Chip | Color | Chip | Color |
| Maltose- tryptone | S | 266 | dark gray | 93 | yellowish gray | 93 | yellowish gray |
| | R | 57 | light brown | 71 | moderate orange yellow | 71 | moderate orange yellow |
| | P | 87 | moderate yellow | 87 | moderate yellow | 87 | moderate yellow |
| Yeast extract- malt extract (ISP-2) | S | 23 | dark red- dish gray | 22 | reddish gray | 63 | light brown- ish gray |
| | R | 57 | light brown | 71 | moderate orange yellow | 71 | moderate orange yellow |
| | P | 71 | moderate orange yellow | 87 | moderate yellow | 87 | moderate yellow |
| Oatmeal (ISP-3) | S | 45 | light gray- ish red- dish brown | 63 | light brown- ish gray | 63 | light brown- ish gray |
| | R | 29 | moderate yellowish pink | 71 | moderate orange yellow | 71 | moderate orange yellow |
| | P | 30 | dark yel- lowish pink | 87 | moderate yellow | 87 | moderate yellow |
| Inorganic Salts Starch (ISP-4) | S | 23 | dark red- dish gray | 63 | light brown- ish gray | 22 | reddish gray |
| | R | 73 | pale orange yellow | 71 | moderate yellow | 71 | moderate yellow |
| | P | 79 | light gray- ish yel- lowish brown | 80 | grayish yellowish brown | 80 | grayish yellowish brown |
| Glycerol- asparagine (ISP-5) | S | 266 | dark gray | 93 | yellow gray | 93 | yellow gray |
| | R | 57 | light brown | 71 | moderate orange yellow | 71 | moderate orange yellow |
| | P | — | — | 87 | moderate yellow | 87 | moderate yellow |

S = Surface
R = Reverse
P = Pigment
*Color determination was made on growth on plates incubated 14 days at 28° C. Color was determined by comparison with NBS color chips [SP 440, Ibid. and SRM 2106, Ibid.]

TABLE 3

Growth on Carbon Compounds in the Synthetic Medium of Shirling and Gottlieb*

| Synthetic Medium (ISP-9) | S. microspinus NRRL 12524 | S. impexus NRRL 3089 | S. fungicidicus ATCC 21013 |
|---|---|---|---|
| Negative Control (No carbon cpd.) | — | — | — |
| Positive Control (D-glucose) | + | ++ | + |
| L-arabinose | ++ | ++ | ++ |
| Sucrose | — | ± | ± |
| D-xylose | ++ | ++ | ++ |
| Inositol | ++ | ++ | ++ |
| D-mannitol | ++ | ++ | ++ |
| D-fructose | + | ++ | ++ |
| Rhamnose | ++ | ++ | ++ |
| Raffinose | — | — | — |
| Cellulose | — | — | — |

++ = Strong utilization
+ = Positive utilization
± = Doubtful utilization
— = No utilization
*Shirling, E. B. et al., Ibid.

TABLE 4

| | | Culture Characteristics - General | | |
|---|---|---|---|---|
| Agar Medium | Deter- mina- tion | S. microspinus NRRL 12524 | S. impexus NRRL 3809 | S. fungicidicus ATCC 21013 |
| Agar | | | | |
| Peptone- iron | S | pale gray | white center; pink-tan edge | gray center; white edge |
| | R | tan | light yellow- tan | yellow |
| | P | — | — | — |
| | O | melanin negative | melanin negative | melanin negative |
| Calcium maleate | S | gray | gray | gray |
| | R | pale gray | gray | gray-yellow |

TABLE 4-continued

Culture Characteristics - General

| Agar Medium | Determination | S. microspinus NRRL 12524 | S. impexus NRRL 3809 | S. fungicidicus ATCC 21013 |
|---|---|---|---|---|
| | P | — | — | — |
| | O | malate not solubilized | malate not solubilized | malate not solubilized |
| Glucose-asparagine | S | gray-pink | yellow vegetative growth | cream-gray |
| | R | pink-tan | deep yellow | deep yellow |
| | P | pale pink | — | — |
| Skim milk | S | brown vegetative growth | gray center; cream edge | trace gray |
| | R | tan | orange | orange |
| | P | tan | orange | orange |
| | O | casein not solubilized | casein solubilized | casein solubilized |
| Tyrosine | S | pale gray | gray center; cream edge | cream center; gray-white edge |
| | R | orange-tan | orange-yellow | orange-tan |
| | P | orange-tan | pale orange | orange-tan |
| | O | tyrosine solubilized | tyrosine solubilized | tyrosine solubilized |
| Xanthine | S | pale gray on edge; tan vegetative center | gray cream | cream |
| | R | yellow-cream | orange | cream |
| | P | pale yellow | — | pale yellow |
| | O | xanthine not solubilized | xanthine not solubilized | xanthine not solubilized |
| Nutrient starch | S | blue-gray | gray center; cream edge | cream |
| | R | yellow cream | yellow | yellow |
| | P | pale yellow | pale yellow | pale yellow |
| | O | starch solubilized | starch partially solubilized | starch partially solubilized |
| Yeast extract-malt extract | S | lavender-gray | gray-cream | gray with cream edge |
| | R | orange-tan | yellow-orange tan | yellow |
| | P | pale orange-tan | pale yellow | pale yellow |
| Peptone-yeast extract-iron (ISP-6) | S | light gray-pink | light gray-white | colorless vegetative with very slight trace gray-white |
| | R | yellow-tan | yellow-tan | yellow-tan |
| | P | yellow-tan | yellow-tan | yellow-tan |
| | O | melanin negative | melanin negative | melanin negative |
| Tyrosine (ISP-7) | S | steel gray | mottled gray-yellow with yellow exudate | light steel gray |
| | R | light gray | yellow-tan | light yellow-gray |
| | P | — | trace yellow-tan | — |
| | O | melanin negative | melanin negative | melanin negative |
| Broth | | | | |
| Synthetic nitrate | S | trace white aerial on surface pellicle | trace white aerial on surface pellicle | slight white aerial on surface pellicle |
| | P | — | — | — |
| | O | fine growth throughout flocculent growth at base growth colorless nitrates not reduced | trace growth throughout flocculent growth at base growth colorless nitrates reduced | slight growth throughout flocculent growth at base growth colorless nitrates reduced |
| Nutrient nitrate | S | gray white aerial on surface pellicle | white aerial on surface pellicle | white aerial on surface pellicle |
| | P | — | — | — |
| | O | flocculent | flocculent | flocculent |

TABLE 4-continued

Culture Characteristics - General

| Agar Medium | Determination | S. microspinus NRRL 12524 | S. impexus NRRL 3809 | S. fungicidicus ATCC 21013 |
|---|---|---|---|---|
| | | yellowish bottom growth nitrates not reduced | yellowish bottom growth nitrates reduced | yellowish bottom growth nitrates reduced |
| Litmus milk | S | trace gray-white aerial on blue-gray surface ring | pale gray-white aerial on surface pellicle blue-gray-tan surface ring | pale gray-white aerial on surface pellicle blue-gray-tan surface ring |
| | P | — | — | — |
| | O | litmus reduced pH 7.7 | litmus reduced pH 7.6 | litmus reduced pH 7.4 |
| Gelatin | | | | |
| Plain | S | trace tan vegetative growth at surface | trace tan vegetative growth at surface | trace tan vegetative growth at surface |
| | P | trace olive | trace yellow | trace yellow |
| | O | liquefaction complete | liquefaction complete | liquefaction complete |
| Nutrient | S | tan vegetative growth at surface | tan vegetative growth at surface | tan vegetative growth at surface |
| | P | — | tan | yellow |
| | O | liquefaction complete | liquefaction complete | liquefaction complete |

S = Surface (aerial growth unless otherwise noted)
R = Reverse
P = Pigment
O = Other Characteristics The compound of the invention process is produced when the elaborating organism is grown in an aqueous nutrient medium under submerged aerobic conditions. It is to be understood, also, that for the preparation of limited amounts surface cultures and bottles can be employed. The organism is grown in a nutrient medium containing a carbon source, for example, an assimilable nitrogen compound or proteinaceous material. Preferred carbon sources include glucose, brown sugar, sucrose, glycerol, starch, cornstarch, lactose, dextrin, molasses, and the like. Preferred nitrogen sources include cornsteep liquor, yeast, autolyzed brewer's yeast with milk solids, soybean meal, cottonseed meal, cornmeal, milk solids, pancreatic digest of casein, fish meal, distiller's solids, animal peptone liquors, meat and bone scraps, and the like. Combinations of these carbon and nitrogen sources can be used advantageously. Trace metals, for example, zinc, magnesium, manganese, cobalt, iron, and the like, need not be added to the fermentation medium since tap water and unpurified ingredients are used as components of the medium prior to sterilization of the medium.

Production of the compound by the invention process can be effected at any temperature conducive to satisfactory growth of the microorganism, for example, between about 18° and 40° C., and preferably between about 20° and 28° C. Ordinarily, optimum production of the compound is obtained in about 3 to 15 days. The medium normally remains alkaline during the fermentation. The final pH is dependent, in part, on the buffers present, if any, and in part on the initial pH of the culture medium.

When growth is carried out in large vessels and tanks, it is preferable to use the vegetative form, rather than the spore form, of the microorganism for inoculation to avoid a pronounced lag in the production of the compound and the attendant inefficient utilization of the equipment. Accordingly, it is desirable to produce a vegetative inoculum in a nutrient broth culture by inoculating this broth culture with an aliquot from a soil, liquid $N_2$ agar plug, or a slant culture. When a young, active vegetative inoculum has thus been secured, it is transferred aseptically to large vessels or tanks. The medium in which the vegetative inoculum is produced can be the same as, or different from, that utilized for the production of the compound, so long as a good growth of the microorganism is obtained.

A variety of procedures can be employed in the isolation and purification of the compound produced by the subject invention from fermentation beers. Isolation can be accomplished by extraction with solvents such as methylene chloride, acetone, butanol, ethyl acetate and the like; and silica gel chromatography can be used to purify crude preparations of the antibiotic.

In a preferred recovery process, the compound produced by the subject process is recovered from the culture medium by separation of the mycelia and undissolved solids by conventional means, such as by filtration or centrifugation and solvent extraction of the filtered broth. The filtrate can be extracted with a solvent for antibiotic U-64,815, for example, methylene chloride, and the extract evaporated under reduced pressure to an aqueous concentrate. This preparation can be purified by chromatography on silica gel. The solvent system used for the chromatography is methylene chloride:methanol (95:5) (v/v) and (90:10). Antibiotic U-64,185 is shown at $R_f$=0.50-0.55 silica gel G plates in $MeCl_2$/MeOH 9:1 using standard bioautography on *Bacillus subtilis*.

The antibiotic of the subject invention also can be recovered from the fermentation broth by resin sorption on a resin comprising a non-ionic macro porous copolymer of styrene cross linked with divinylbenzene. Suitable resins are Amberlite XAD-2, XAD-4, and XAD-7, according to the procedure disclosed in U.S. Pat. No. 3,515,717. (Amberlite resins are available from Rohm and Haas, Philadelphia, PA). The antibiotic can be eluted from said resins by using acetone.

Salts of antibiotic U-64,815 also can be formed with inorganic or organic bases. Such salts can be prepared, as for example, by suspending antibiotic U-64,815 in water, adding a dilute base until the pH of the suspension is about 10.0 to 11.0, and freeze-drying to provide a dried residue consisting of the U-64,815 salt. Antibiotic U-64,815 salts with inorganic cations which can be formed include the sodium, potassium, and calcium salts. Other salts of U-64,815, including those with inorganic bases such as primary, secondary, and tertiary monoamines as well as with polyamines, also can be formed using the above-described or other commonly employed procedures. Other valuable salts are obtained with therapeutically effective bases which impart additional therapeutic effects thereto. Such bases are, for example the purine bases such as theophyllin, theobromine, caffeine, or derivatives of such purine bases; antihistaminic bases which are capable of forming salts with weak acids, pyridine compounds such as nicotinic acid amide, isonicotinic acid hydrazide, and the like; phenylalkylamines such as adrenaline, ephedrine, and the like; choline, and others. Salts of U-64,815 can be used for the same biological purposes as the parent compound.

The following examples are illustrative of the process and product of the invention, but are not to be construed as limiting. All percentages are by weight and all solvent mixture proportions are by volume unless otherwise noted.

EXAMPLE 1

A. Fermentation

A biologically pure culture of *Streptomyces microspinus*, NRRL 12524, is used to inoculate 500-ml Erlenmeyer seed flasks containing 100 ml of sterile medium consisting of the following ingredients:

|  | g/liter |
| --- | --- |
| Cerelose | 25 |
| Pharmamedia* | 25 |
| Deionized water q.s. | 1 liter |

*Pharmamedia is an industrial grade of cottonseed flour produced by Traders Oil Co, Fort Worth, TX.

The seed medium post-sterilization pH is ~6.5. The seed inoculum is grown for three days at 28° C. on a Gump rotary shaker operating at 250 rpm and having a 2½ inch stroke.

Seed inoculum (100 ml), prepared as described above, is used to inoculate 500-ml fermentation flasks (Erlenmeyer) containing 100 ml of sterile fermentation medium consisting of the following ingredients:

|  | g/liter |
| --- | --- |
| Cerelose | 10 |
| Bacto-Peptone (Difco) | 5 |
| Black Strap Molasses* | 20 |
| Tap Water | Balance |

*Supplied by Knappen Milling Co., Augusta, MI.

The pH is adjusted to 7.2 with NaOH before autoclaving.

The inoculated fermentation medium is incubated at a temperature of 28° C. for 5 days on a Gump rotary shaker operating at 250 rpm and having a 2½ inch stroke.

A typical five-day fermentation has the following titers of antibiotic in the fermentation broth:

| Day | Assay, BU/ml |
| --- | --- |
| 2 | 8.0 |
| 3 | >16 |
| 4 | >16 |
| 5 | >16 |

The assay is a *Bacillus subtilis* disc plate assay using 0.1 M potassium phosphate buffer, pH 5.0 as diluent.

B. Recovery

Whole beer, from a fermentation as described above, is filtered and adjusted to neutral pH with HCl and filtered with 5% diatomaceous earth (wt/v). The clear beer is then defatted with two half volumes of Skellysolve B (isomeric hexanes). The defatted beer is then extracted with two half volumes of methylene chloride and these extracts are combined and reduced in volume.

1-liter whole beer adj. to pH 7 with HCl

↓ filtered with 5% Dicalite (diatomaceous earth)

Clear Beer

| (¼" dipped disc bioassay) Organism | Whole Beer Zone (mm) | Clear Beer Zone (mm) |
| --- | --- | --- |
| B. subtilis | 29 | 29 |
| M. luteus | 25 | 24 |
| C. perfringens | 28 | 28 |

| Organism | 1st Extract | 2nd Extract | Combined Extracts | Spent Beer |
| --- | --- | --- | --- | --- |
| Skellysolve B | | | | |
| B. subtilis | 0 | 0 | 0 | 28 |
| M. luteus | 0 | 0 | 0 | 23 |
| C. perfringens | 0 | 0 | 0 | 27 |
| $Me_2Cl_2$ | | | | |
| B. subtilis | 27 | 19 | 27 | 21 |
| S. lutea | 23 | 0 | 21 | 16 |
| C. perfringens | 27 | 18 | 27 | 20 |

C. Purification

A 21.5 g sample of a $CH_2Cl_2$ extract, prepared as described above, is dissolved in a minimal volume of $CH_2Cl_2$ and passed onto the head of a 5' column packed with 1400 g of Merck Silica Gel 60 slurried in $CH_2Cl_2$. A flow rate of ca. 7 ml/min is established with a solvent of $CH_2Cl_2$/MeOH; 90/5; 20 ml fractions are collected. After 8.7 liters, the solvent is changed to $CH_2Cl_2$/MeOH; 90/10.

Fractions are analyzed by thin layer chromatography (TLC) using Analtech Silica gel GF plates run in $CH_2Cl_2$/MeOH, 9/1. The component of interest is first detected by quenching under U.V. 254 nm light followed by spraying with a p-anisaldehyde reagent ($EtOH:H_2SO_4$:Acetic Acid:p-anisaldehyde, 90:5:1:5) and heating. U-64,815 runs in this system with $R_f$=0.50–0.55 and develops a deep purple coloration when processed with this reagent.

Fractions 436-570 are pooled to give 4.25 g of a brown solid which has ~32 bu/mg when assayed with ¼" discs on *B. subtilis* by a dilution bioassay. (One bu is defined as the amount of antibiotic needed to produce a 20 mm zone).

The 4.25 g solid is dissolved in a minimal volume of MeOH/H$_2$O, 80/20 and loaded onto the head of a 25 mm I.D. column packed with 42.5 g of Whatman LRP-1 reverse phase equilibrated with the solvent. A flow rate of 1.5 ml/min is established with MeOH/H$_2$O, 80/20 while 50 ml fractions are collected. After the seventh fraction, the solvent is changed to 100% MeOH. Fractions are analyzed in the identical manner as before and also with dipped discs plated against *B. subtilis*. The active fractions containing the best material as seen by TLC are pooled and reduced in volume to give 2.75 g of an off-white powder of essentially pure antibiotic U-64,815.

We claim:

1. A process for preparing antibiotic U-64,815, which in its essentially pure form has the following characteristics:
   (a) molecular weight range of 1,104–1,324;
   (b) molecular formula: $C_{60-65}H_{82-102}N_{1-3}O_{18-25}$;
   (c) is insoluble in water and hexane, soluble in methanol, acetone, methylene chloride, ethanol, and dimethylsulfoxide;
   (d) a characteristic $^{13}$C-NMR spectrum as shown in FIG. 3 of the drawings;
   (e) a characteristic UV spectrum as shown in FIG. 2 of the drawings; and,
   (f) a characteristic infrared absorption spectrum when dissolved in a mineral oil mull as shown in FIG. 1 of the drawings;

which comprises cultivating *Streptomyces microspinus*, having the identifying characteristics of NRRL 12524, in an aqueous nutrient medium under aerobic conditions until substantial antibiotic U-64,815 activity is imparted to said medium.

2. A process, according to claim 1, wherein said aqueous nutrient medium contains a source of assimilable carbohydrate and assimilable nitrogen.

* * * * *